(12) United States Patent
Hamada et al.

(10) Patent No.: US 9,687,212 B2
(45) Date of Patent: Jun. 27, 2017

(54) ULTRASONIC DIAGNOSIS APPARATUS, ULTRASONIC IMAGE PROCESSING APPARATUS, ULTRASONIC IMAGE PROCESSING METHOD, AND ULTRASONIC IMAGE PROCESSING PROGRAM

(75) Inventors: Kenji Hamada, Otawara (JP); Yoshitaka Mine, Nasushiobara (JP)

(73) Assignee: Toshiba Medical Systems Corporation, Otawara-shi (JP)

( * ) Notice: Subject to any disclaimer, the term of this patent is extended or adjusted under 35 U.S.C. 154(b) by 753 days.

(21) Appl. No.: 12/899,945

(22) Filed: Oct. 7, 2010

(65) Prior Publication Data
US 2011/0087102 A1 Apr. 14, 2011

(30) Foreign Application Priority Data
Oct. 8, 2009 (JP) .................................. 2009-234271

(51) Int. Cl.
*A61B 8/00* (2006.01)
*A61B 8/06* (2006.01)
(Continued)

(52) U.S. Cl.
CPC ................ *A61B 8/469* (2013.01); *A61B 8/06* (2013.01); *A61B 8/13* (2013.01); *A61B 8/463* (2013.01); *A61B 8/0866* (2013.01); *A61B 8/467* (2013.01)

(58) Field of Classification Search
CPC .... A61B 8/00; A61B 8/13; A61B 5/00; A61B 5/107; G01T 1/66; G06K 9/00
(Continued)

(56) References Cited

U.S. PATENT DOCUMENTS 6,526,163 B1 * 2/2003 Halmann et al. ............. 382/128
2003/0097068 A1 * 5/2003 Hossack et al. .............. 600/443
(Continued)

FOREIGN PATENT DOCUMENTS

JP 9-262236 10/1997
JP 2001-145631 5/2001
(Continued)

OTHER PUBLICATIONS

Office Action issued Jan. 21, 2014, in Japanese Patent Application No. 2010-181859 (with English-language tanslation).

*Primary Examiner* — Joseph M Santos Rodriguez
(74) *Attorney, Agent, or Firm* — Oblon, McClelland, Maier & Neustadt, L.L.P.

(57) ABSTRACT

According to one embodiment, an ultrasonic diagnosis apparatus executes B-mode scanning and color Doppler mode scanning on a scanning region associated with an interior of the womb of a pregnant woman via an ultrasonic probe. A first generating unit generates first color Doppler mode data and generates first B-mode data. A specifying unit specifies a specific region including at least one of an amniotic fluid region and a fetus region based on one of a signal intensity distribution and a luminance distribution of the first B-mode data. A second generating unit generates second color Doppler mode data by deleting a specific data from the first color Doppler mode data. The specific color Doppler mode data corresponds to the specific region. A display unit displays a color Doppler mode image and a first B-mode image while superimposing the color Doppler mode image and the first B-mode image.

19 Claims, 6 Drawing Sheets

(51) Int. Cl.
*A61B 8/13* (2006.01)
*A61B 8/08* (2006.01)

(58) Field of Classification Search
USPC ....... 600/313, 338, 351, 407, 437, 443, 453; 382/128
See application file for complete search history.

(56) References Cited

U.S. PATENT DOCUMENTS

| | | | |
|---|---|---|---|
| 2005/0228278 A1* | 10/2005 | Chalana et al. | 600/437 |
| 2006/0247506 A1* | 11/2006 | Balberg et al. | 600/323 |
| 2008/0114244 A1* | 5/2008 | Murashita et al. | 600/443 |
| 2008/0188751 A1* | 8/2008 | Sato | 600/454 |
| 2009/0024029 A1* | 1/2009 | Murashita | 600/437 |
| 2009/0036749 A1* | 2/2009 | Freiburger et al. | 600/300 |
| 2009/0078875 A1* | 3/2009 | Rousso et al. | 250/363.04 |
| 2009/0093717 A1* | 4/2009 | Carneiro et al. | 600/443 |

FOREIGN PATENT DOCUMENTS

| | | |
|---|---|---|
| JP | 2005-143836 | 6/2005 |
| JP | 2006-223712 | 8/2006 |
| JP | 2009-78016 | 4/2009 |

\* cited by examiner

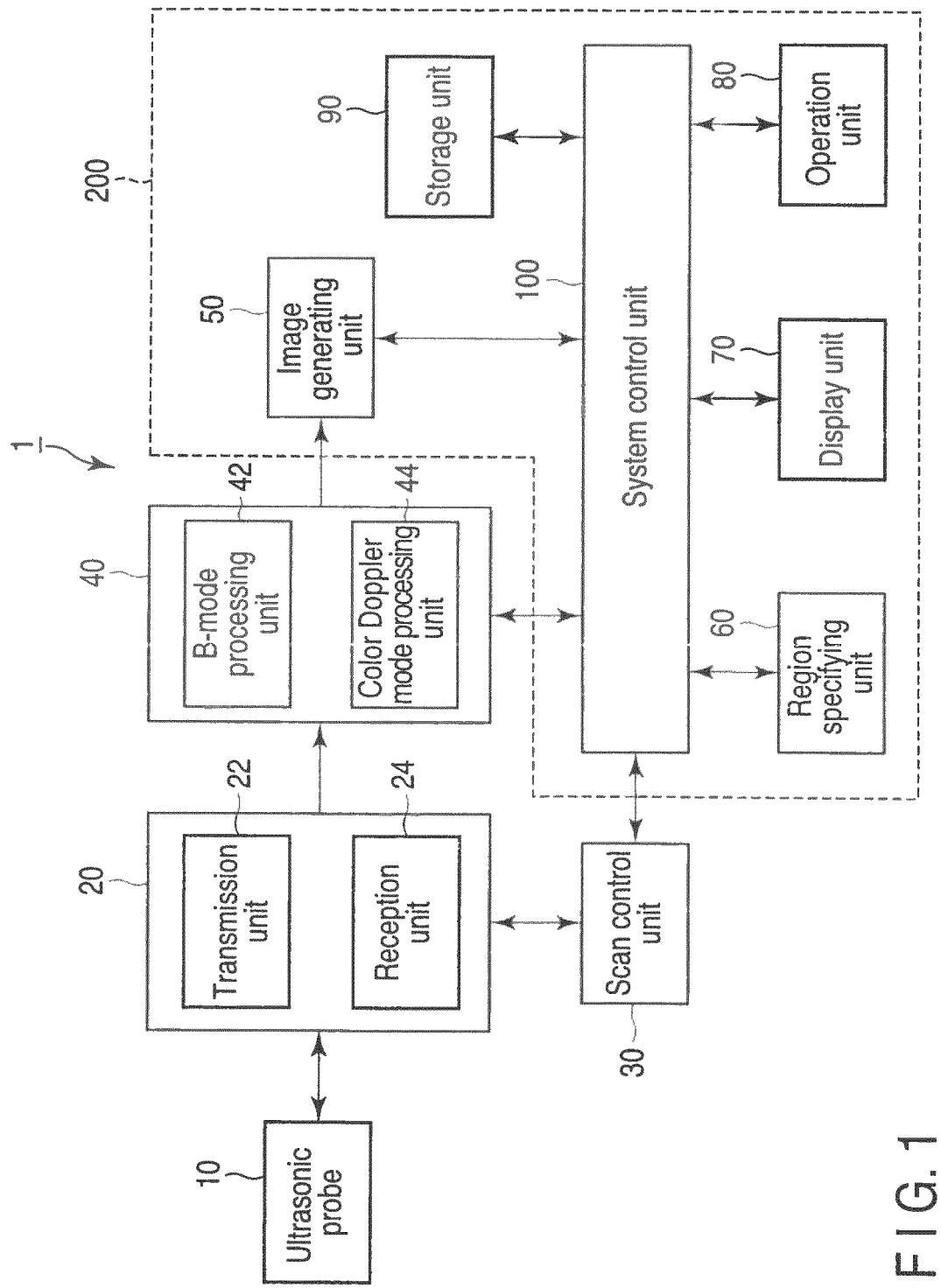
F I G. 1

ULTRASONIC DIAGNOSIS APPARATUS, ULTRASONIC IMAGE PROCESSING APPARATUS, ULTRASONIC IMAGE PROCESSING METHOD, AND ULTRASONIC IMAGE PROCESSING PROGRAM

CROSS-REFERENCE TO RELATED APPLICATIONS

This application is based upon and claims the benefit of priority from Japanese Patent Application No. 2009-234271, filed Oct. 8, 2009; the entire contents of which are incorporated herein by reference.

FIELD

Embodiments described herein relate generally to an ultrasonic diagnosis apparatus, ultrasonic image processing apparatus, ultrasonic image processing method, and ultrasonic image processing program.

BACKGROUND

A color Doppler mode image expresses fluid object information of a fluid object such as a blood flow, e.g., velocity, power, and variance components, in color, by using the color Doppler method. At the time of ultrasonic examination, a color Doppler mode image is superimposed and displayed on a B-mode image.

Antenatal ultrasonic examination is performed by using these techniques. As an example of an application of the internal ultrasonic examination method, there is available a technique of displaying a three-dimensional image of a fetus in the womb.

In performing antenatal ultrasonic examination, a doctor detects an intraplacental blood flow, diagnoses fetal development or a placental state, or checks the presence/absence of a disease such as an arteriovenous shunt. At the time of antenatal ultrasonic examination, the amniotic fluid moves due to the movement of a fetus or the like. In this case, the fluid object information of the moving amniotic fluid overlaps a placental cortex portion or the like on an image. It is therefore difficult to observe a blood vessel in the placental cortex portion. In addition, when the fetus is close to the placenta, it is very difficult to observe the placenta.

BRIEF DESCRIPTION OF THE DRAWINGS

FIG. 1 is a block diagram showing the arrangement of an ultrasonic diagnosis apparatus according to this embodiment;

DETAILED DESCRIPTION

Figure 2:
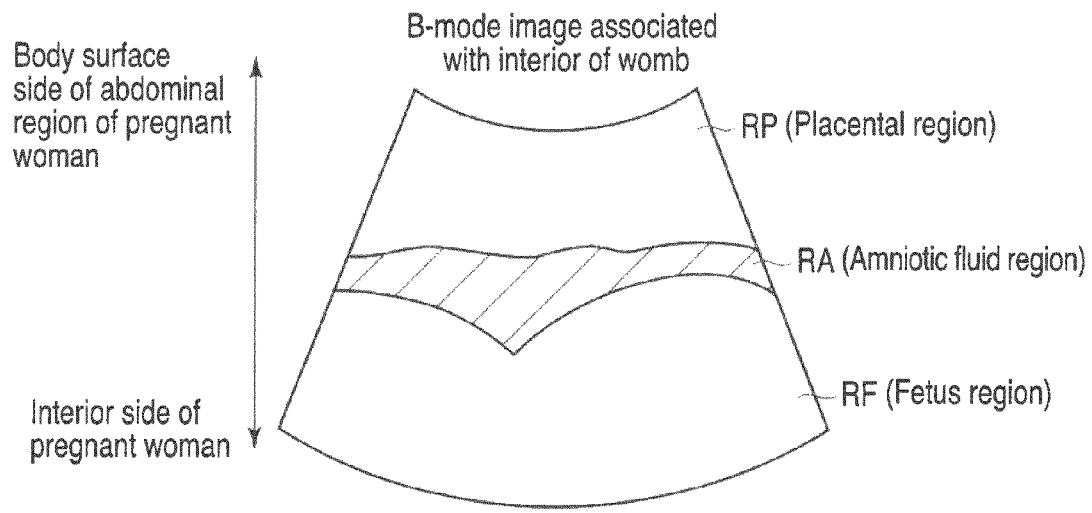
FIG. 2 is a view showing an example of a B-mode image associated with the interior of the womb, which is generated by an image generating unit in FIG. 1.

In general, according to one embodiment, an ultrasonic diagnosis apparatus executes B-mode scanning and color Doppler mode scanning on a scanning region associated with the interior of the womb of a pregnant woman via an ultrasonic probe. The ultrasonic diagnosis apparatus according to this embodiment includes a first generating unit, specifying unit, second generating unit, and display unit. The first generating unit generates first color Doppler mode data associated with the scanning region based on an output from the ultrasonic probe at the time of the color Doppler mode scanning and generate first B-mode data associated with the scanning region based on an output from the ultrasonic probe at the time of the B-mode scanning. The specifying unit specifies a specific region including at least one of an amniotic fluid region and a fetus region based on one of a signal intensity distribution and a luminance distribution of the first B-mode data. The second generating unit generates second color Doppler mode data by deleting a specific data from the first color Doppler mode data. The specific color Doppler mode data corresponds to the specific region. The display unit displays a color Doppler mode image and a first B-mode image while superimposing the color Doppler mode image and the first B-mode image. The color Doppler mode image corresponds to the second color Doppler mode data. The first B-mode image corresponds to the first B-mode data.

The ultrasonic diagnosis apparatus, ultrasonic image processing apparatus, and ultrasonic image processing program according to this embodiment will be described below with reference to the views of the accompanying drawing.

The ultrasonic diagnosis apparatus, ultrasonic image processing apparatus, and ultrasonic image processing program according to this embodiment are provided for ultrasonic examination of a woman before delivery. A subject in this embodiment is therefore a pregnant woman. In general, a fetus is surrounded by the amnion in the womb (uterus). A region surrounded by the amnion is filled with amniotic fluid. A placenta is formed on the intrauterine wall. Assume that an ultrasonic scanning region in this embodiment is the interior of the womb including a fetus, amniotic fluid, and placenta.

FIG. 1 is a block diagram showing the arrangement of an ultrasonic diagnosis apparatus 1 according to this embodiment. As shown in FIG. 1, the ultrasonic diagnosis apparatus 1 according to the embodiment includes an ultrasonic probe 10, a transmission/reception unit 20, a scan control unit 30, a signal processing unit 40, an image generating unit 50, a region specifying unit 60, a display unit 70, an operation unit 80, a storage unit 90, and a system control unit 100. Note that the image generating unit 50, the region specifying unit 60, the display unit 70, the operation unit 80, the storage unit 90, and the system control unit 100 constitute an ultrasonic image processing apparatus 200 according to the embodiment.

The ultrasonic probe 10 receives drive pulses from the transmission/reception unit 20 and transmits ultrasonic waves to a scanning region in the subject. The transmitted ultrasonic waves are sequentially reflected by the discontinuity (echo source) of acoustic impedance of the internal body tissue. The ultrasonic probe 10 receives the reflected ultrasonic waves. The ultrasonic probe 10 converts the received ultrasonic waves into an echo signal (electrical signal), and supplies it to the transmission/reception unit 20.

The transmission/reception unit 20 repetitively transmits and receives ultrasonic waves to and from the scanning region via the ultrasonic probe 10 under the control of the scan control unit 30. More specifically, the transmission/reception unit 20 includes a transmission unit 22 and a reception unit 24.

The transmission unit 22 repetitively supplies drive pulses to the transducers in the ultrasonic probe 10 with the delay times assigned to the respective transducers under the control of the scan control unit 30. Upon receiving the supplied drive pulses, the transmission unit 22 transmits ultrasonic beams in a predetermined transmission direction via the ultrasonic probe 10. More specifically, the transmission unit 22 repetitively generates rate pulses for each transducer at a predetermined rate frequency fr Hz (period: 1/fr sec). The transmission unit 22 gives each rate pulse the delay time required to form a transmission beam associated with a predetermined transmission direction and a predetermined transmission focal position. The transmission unit 22 then generates a drive pulse at the timing based on each delayed rate pulse, and supplies the generated drive pulse to each transducer. Upon receiving the supplied drive pulse, each transducer generates an ultrasonic wave. With this operation, the ultrasonic probe 10 transmits an ultrasonic beam focused at the predetermined transmission focal position in the predetermined transmission direction.

The reception unit 24 repetitively receives the ultrasonic waves reflected inside the scanning region as echo signals via the ultrasonic probe 10 under the control of the scan control unit 30. Upon receiving the ultrasonic waves, the reception unit 24 forms a reception beam. More specifically, the reception unit 24 receives an echo signal from the ultrasonic probe 10, and amplifies the received echo signal. The reception unit 24 then converts the amplified echo signal from an analog signal to a digital signal. The reception unit 24 stores the digitally converted echo signal in a digital memory. Such a digital memory is provided for, for example, each transducer. The echo signal is stored in the digital memory corresponding to the transducer from which the signal has been received, at an address corresponding to the reception time of the echo signal. The reception unit 24 delays and adds the echo signals stored in the digital memories to form an echo signal (to be referred to as a reception signal hereinafter) corresponding to the reception beam from the predetermined direction. More specifically, the reception unit 24 reads out and adds echo signals from addresses corresponding to predetermined reception focal positions. The reception unit 24 generates a reception signal corresponding to the reception beam from the predetermined direction by repeating this delay addition processing while changing the reception focal position along ultrasonic scanning lines. The reception signal is supplied to the signal processing unit 40. Note that the stage at which an echo signal is analog/digital-converted is not limited to that described above. Such conversion may be performed at any of the existing stages.

The scan control unit 30 controls the transmission unit 22 and the reception unit 24 in accordance with a predetermined scan sequence to execute B-mode scanning and color Doppler mode scanning on a scanning region. For example, the scan control unit 30 alternately performs B-mode scanning and color Doppler mode scanning for each scanning surface. Note that a scanning region may be two-dimensional or three-dimensional spatial region. Scanning on a three-dimensional spatial region uses a method of transmitting and receiving ultrasonic beams using a two-dimensional array of transducers or a method of transmitting and receiving ultrasonic beams while mechanically swinging a one-dimensional array of transducers. For the sake of a concrete description, assume that a scanning region is a three-dimensional spatial region.

The signal processing unit 40 performs B-mode processing corresponding to B-mode scanning and color Doppler mode processing corresponding to color Doppler mode scanning based on a reception signal from the reception unit 24. More specifically, the signal processing unit 40 includes a B-mode processing unit 42 and a color Doppler mode processing unit 44.

The B-mode processing unit 42 generates B-mode signal data associated with a scanning region by performing B-mode processing of a reception signal from the reception unit 24 at the time of B-mode scanning.

More specifically, the B-mode processing unit 42 detects the envelope of the reception signal and logarithmically compresses the envelope-detected reception signal. This generates the B-mode signal data representing the intensity of the reception signal with luminance (tone). The generated B-mode signal data is supplied to the image generating unit 50 and the storage unit 90.

The color Doppler mode processing unit 44 generates color Doppler mode signal data associated with a scanning region by performing color Doppler mode processing of a reception signal from the reception unit 24 at the time of color Doppler mode scanning. More specifically, the color Doppler mode processing unit 44 performs quadrature detection of a reception signal, and frequency analysis of the reception signal having undergone quadrature detection, thereby calculating fluid object information such as an average velocity value, variance value, and power value associated with a fluid object such as blood or amniotic fluid at each point in a scanning region. The color Doppler mode processing unit 44 generates the color Doppler mode signal data expressing calculated fluid object information in color. The generated color Doppler mode signal data is supplied to the image generating unit 50 and the storage unit 90.

The image generating unit 50 generates B-mode image data associated with a scanning region based on a B-mode signal data from the B-mode processing unit 42 or the storage unit 90. For example, the image generating unit 50 generates a two-dimensional B-mode image data associated with one scanning surface in a scanning region based on a B-mode signal. The image generating unit 50 also generates three-dimensional B-mode image data (to be referred to as B-mode volume data hereinafter) associated with a plurality of scanning surfaces in a scanning region. In this case, the image generating unit 50 generates the two-dimensional B-mode image data associated with an arbitrary slice by performing MPR processing of generated B-mode volume data. The image generating unit 50 generates two-dimensional B-mode image data (so-called three-dimensional image data) at an arbitrary viewpoint position and in an arbitrary visual line direction by performing three-dimensional image processing such as pixel value projection processing or volume rendering for B-mode volume data. A B-mode image is an image expressing the signal intensity distribution of a B-mode signal in a scanning region with luminance. The generated B-mode image data is supplied to the region specifying unit 60 and the storage unit 90.

Likewise, the image generating unit 50 generates color Doppler mode image data associated with a scanning region based on a color Doppler mode signal from the color Doppler mode processing unit 44 or the storage unit 90. For example, the image generating unit 50 generates two-dimensional color Doppler mode image data associated with one scanning surface in a scanning region based on a color Doppler mode signal. The image generating unit 50 also generates three-dimensional color Doppler mode image data (to be referred to as color Doppler mode volume data hereinafter) associated with a plurality of scanning surfaces in a scanning region based on a color Doppler mode signal. In this case, the image generating unit 50 generates the two-dimensional color Doppler mode image data associated with an arbitrary slice by performing MPR processing of the generated color Doppler mode volume data. Alternatively, the image generating unit 50 may generate the two-dimensional color Doppler mode image data (so-called three-dimensional image data) at an arbitrary viewpoint position and in an arbitrary visual line direction by performing three-dimensional image processing such as pixel value projection processing or volume rendering for color Doppler mode volume data. A color Doppler mode image is an image expressing fluid object information in a scanning region in color. The generated color Doppler mode image data is supplied to the region specifying unit 60 and the storage unit 90.

Note that data at a stage before the image generating unit 50 is called raw data, and data at a stage after the image generating unit 50 is called image data. The data of a reception signal, the data of a B-mode signal, and the data of a B-mode image at the time of B-mode scanning will be generically referred to as B-mode data. A reception signal, the data of a color Doppler mode signal, and the data of a color Doppler mode image at the time of color Doppler mode scanning will be generically referred to as color Doppler mode data.

The region specifying unit 60 specifies a data region (to be referred to as an amniotic fluid region hereinafter) having a signal intensity distribution or luminance distribution corresponding to the amniotic fluid or a data region (to be referred to as a fetus region hereinafter) having a signal intensity distribution or luminance distribution corresponding to a fetus from B-mode data based on the signal intensity distribution or luminance distribution of the B-mode data. An amniotic fluid and a fetus region are regions which visually inhibit the observation of the placenta, especially a blood flow in a placental cortex portion, on an image. If, for example, there is no need to discriminate an amniotic fluid region from a fetus region, a region including an amniotic fluid region and a fetus region will be referred to as an inhibition region. The position data of a specified inhibition region is supplied to the image generating unit 50. Inhibition region specifying processing by the region specifying unit 60 will be described in detail later.

The image generating unit 50 generates image data by deleting a first inhibition data from the color Doppler mode image data. The generated image data will be referred to as a deletion color Doppler mode image data hereinafter. The first inhibition data corresponds to the inhibition region. The generated deletion color Doppler mode image data is supplied to the display unit 70. The image generating unit 50 generates image data by deleting a second inhibition data from the B-mode image data. The generated image data will be referred to as a deletion B-mode image data hereinafter. The second inhibition data corresponds to the inhibition data. The generated deletion B-mode image data is supplied to the display unit 70. The normal color Doppler mode image data from which the first inhibition data is not deleted will be simply referred to as the color Doppler mode image data hereinafter. The normal B-mode image data from which the first inhibition data is not deleted will be simply referred to as the B-mode image data hereinafter.

The display unit 70 displays a deletion color Doppler mode image corresponding to the deletion color Doppler mode image data on a display device.

Typically, the display unit 70 displays the deletion color Doppler mode image and a B-mode image while superimposing the deletion color Doppler mode image and the B-mode image. The B-mode image corresponds to the B-mode image data. The display unit 70 may display the deletion color Doppler mode image and a deletion B-mode image while superimposing the deletion color Doppler mode image and the deletion B-mode image. The deletion B-mode image corresponds to the deletion B-mode image data. In this manner, the display unit 70 displays the deletion color Doppler mode image and the deletion B-mode image from which an inhibition region such as an amniotic fluid region or fetus region is removed. As a consequence, the display unit 70 displays the deletion color Doppler mode image and deletion B-mode image in which a pixel region corresponding to the placenta (to be referred to as a placental region hereinafter) is highlighted. Note that the deletion color Doppler mode image and a B-mode image (also deletion B-mode image), which are to be superimposed and displayed on each other, are almost equal in slice position and direction or viewpoint position and visual line direction. As a display device, for example, a CRT display, liquid crystal display, organic EL display, plasma display, or the like can be used.

The operation unit 80 accepts instructions and information input from the user via an input device. As an input device, a keyboard, mouse, various switches, touch panel, or the like can be used.

The storage unit 90 stores B-mode signal data and color Doppler mode signal data from the signal processing unit 40 and the B-mode image data and the color Doppler mode image data from the image generating unit 50. The storage unit 90 stores B-mode signal data, B-mode image data, color Doppler mode signal data, and color Doppler mode image data in association with scanning times. The storage unit 90 also stores an ultrasonic image processing program for highlighting display processing of a placental region.

The system control unit 100 functions as the nerve center of the ultrasonic diagnosis apparatus 1. The system control unit 100 reads out an ultrasonic image processing program from the storage unit 90 and develops the program in the memory. The system control unit 100 controls the respective units in accordance with the developed ultrasonic image processing program to perform highlighting display processing of a placental region.

An example of the operation of this embodiment will be described below. The following description is an example of processing image data (B-mode image data and color Doppler mode image data) constituted by pixels having pixel values corresponding to luminance values. However, this embodiment is not limited to this, and may process raw data (a B-mode signal data and color Doppler mode signal data) having a signal intensity corresponding to a luminance value.

Inhibition region specifying processing by the region specifying unit 60 will be described in detail first. FIG. 2 is a view showing an example of a B-mode image associated with the interior of the womb. As shown in FIG. 2, a B-mode image associated with the interior of the womb includes a placental region RP associated with the placenta, an amniotic fluid region RA associated with amniotic fluid, and a fetus region RF associated with a fetus in increasing order of distance from the surface of an abdominal region. The amniotic fluid region RA is located between the placental region RP and the fetus region RF. In general, the fetus region RF is located near the placental region RP. The placenta is a homogeneous parenchyma. For this reason, the placental region RP exhibits a smaller change in luminance than the amniotic fluid region RA and the fetus region RF. The intensity of a reception signal originating from ultrasonic waves reflected by amniotic fluid is weaker than that of reception signals originating from ultrasonic waves reflected by the placenta and the fetus. For this reason, the amniotic fluid region RA exhibits smaller luminance values than the placental region RP and the fetus region RF. A fetus is formed from various tissues, and hence the intensity of a reception signal originating from ultrasonic waves reflected by the fetus varies more than that of reception signals originating from ultrasonic waves reflected by the placenta and amniotic fluid. For this reason, the fetus region RF exhibits larger changes in luminance than the amniotic fluid region RA and the placental region RP.

The region specifying unit 60 specifies an inhibition region such as an amniotic fluid region or a fetus region on a B-mode image by using the respective luminance distributions of the amniotic fluid, placenta, and fetus. This embodiment will exemplify the following five typical specifying methods. As described above, inhibition region specifying processing is performed for a B-mode image. The specifying processing can also be applied to a two-dimensional B-mode image and a three-dimensional B-mode image (i.e., B-mode volume data). For the sake of a concrete description, assume that inhibition region specifying processing is performed for a two-dimensional B-mode image.

(Specifying Method 1)

The first method is a method of specifying inhibition regions based on statistical indicators indicating the variation degrees of luminance values on a B-mode image. It is preferable to set, as a statistical indicator, a variance value or standard deviation indicating the variation degree of luminances in a predetermined region. For the sake of a concrete description, assume that a statistical indicator indicating a variation degree is a variance value.

As described above, a placental region exhibits a smaller change in luminance than an amniotic fluid region and a fetus region. Therefore, the placental region exhibits smaller variance values than the amniotic fluid region and the fetus region. In specifying method 1, the region specifying unit 60 specifies inhibition regions (both the amniotic fluid region and the fetus region) from the B-mode image by using this characteristic. A typical procedure for inhibition region specifying processing using specifying method 1 will be described below.

Figure 3:
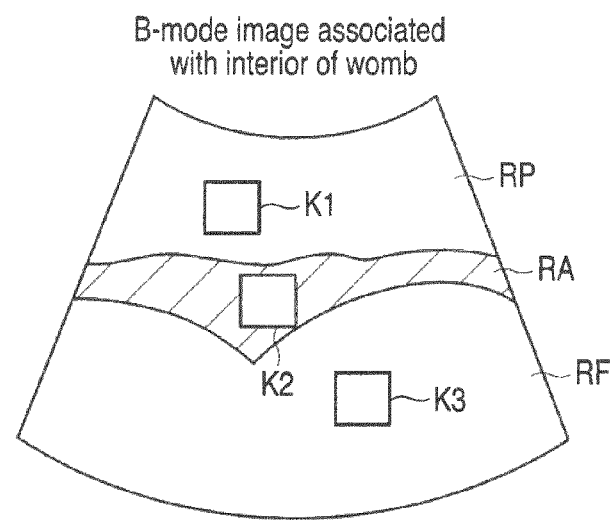
FIG. 3 is a view for explaining inhibition region specifying processing using specifying method 1, which is performed by a region specifying unit in FIG. 1.

FIG. 3 is a view for explaining inhibition region specifying processing using specifying method 1. First of all, the region specifying unit 60 sets a plurality of local regions K at a plurality of positions on a B-mode image. Referring to FIG. 3, assume that first, second, and third local regions K1, K2, and K3 are respectively set in the placental region RP, the amniotic fluid region RA, and the fetus region RF. The local regions K1, K2, and K3 each have, for example, a matrix size of 16×16, which is smaller than the matrix size of a standard B-mode image. The set positions of the local regions K1, K2, and K3 and the number of local regions to be set are automatically or arbitrarily set by the user via the operation unit 80. Note that although FIG. 3 shows the three local regions K1, K2, and K3, local regions are typically set on a B-mode image without any spaces between them.

When local regions are set, the region specifying unit 60 calculates the variance value of luminance values in each local region. Upon calculating the variance value in each local region, the region specifying unit 60 specifies a local region having a variance value equal to or more than a threshold as an inhibition region. The threshold is set in advance between the variance value in an inhibition region (more specifically, a smaller one of the variance value in an amniotic fluid region and the variance value in a fetus region) and the variance value in a placental region. Therefore, any local region having a variance value equal to or more than the threshold belongs to an inhibition region. In the case shown in FIG. 3, for example, the variance value in the first local region K1 is equal to or less than the threshold, and the variance values in the second and third local regions K2 and K3 each are equal to or more than the threshold. Therefore, the second and third local regions K2 and K3 are specified as inhibition regions. The data of the coordinate positions of the inhibition regions are supplied to the image generating unit 50. As described above, according to specifying method 1, both the amniotic fluid region and the fetus region are specified as inhibition regions.

(Specifying Method 2)

The second method is a method of specifying inhibition regions based on anatomical positions and luminance values on a B-mode image.

As described above, a placental region, an amniotic fluid region, and a fetus region are arranged on a B-mode image associated with the interior of the womb in the order named starting from the body surface of an abdominal region of a pregnant woman. That is, the amniotic fluid region and the fetus region are distributed at deeper positions than the placental region. In addition, the placental region, amniotic fluid region, and fetus region belong to different luminance bands.

Figure 4:
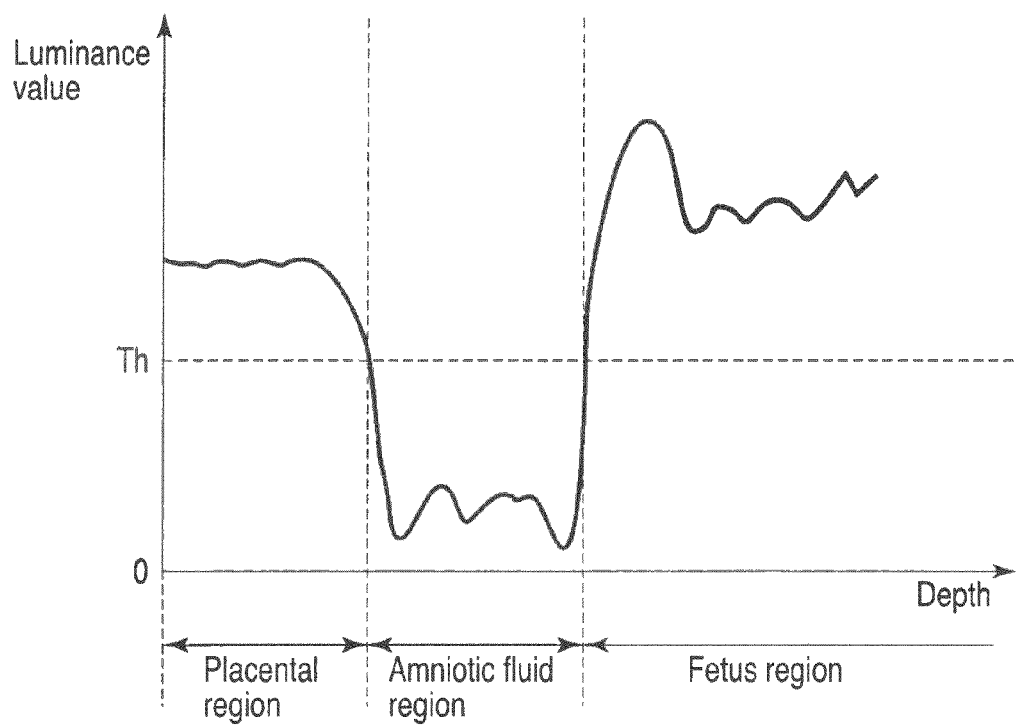
FIG. 4 is a graph showing the relationship between the depth positions and the luminance values on the scanning lines (raster lines) of a B-mode image associated with the interior of the womb, which is generated by the image generating unit in FIG. 1.

FIG. 4 is a graph showing the relationship between depth positions and luminance values on scanning lines (raster lines) of a B-mode image associated with the interior of the womb. As shown in FIG. 4, a placental region, an amniotic fluid region, and a fetus region are distributed on a B-mode image in the order named starting from the surface of an abdominal region of the pregnant woman. The placental region exhibits small changes in luminance in correspondence with the depth positions, whereas the amniotic fluid region and the fetus region exhibit large changes in luminance in correspondence with the depth positions. The luminance bands of the placental region and fetus region each are higher than the luminance band of the amniotic fluid region. In specifying method 2, the region specifying unit 60 specifies inhibition regions (both the amniotic fluid region and the fetus region) from the B-mode image by using this characteristic. A typical procedure for inhibition region specifying processing using specifying method 2 will be described below.

Figure 5:
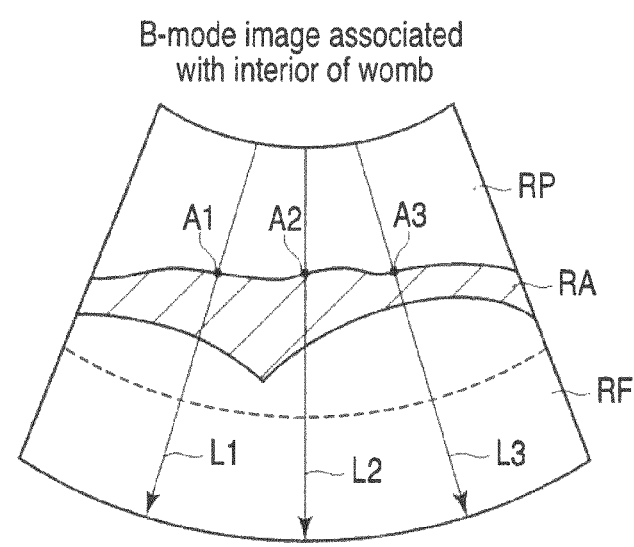
FIG. 5 is a view for explaining inhibition region specifying processing using specifying method 2, which is performed by the region specifying unit in FIG. 1.

FIG. 5 is a view for explaining inhibition region specifying processing using specifying method 2. First of all, the region specifying unit 60 searches pixels from the body surface of an abdominal region to the interior of the body along a scanning line L, and specifies pixels (to be referred to as boundary pixels hereinafter) having luminance values equal to or less than a threshold Th. The threshold Th is set to a value within this luminance range automatically or arbitrarily set by the user via the operation unit 80. Setting the threshold Th in this manner will specify, for example, a pixel A1 positioned on the boundary between the placental region RP and the amniotic fluid region RA in the case of a scanning line L1. In this manner, the region specifying unit 60 searches the pixels on all the scanning lines on the B-mode image to specify boundary pixels. Upon searching on all the scanning lines, the region specifying unit 60 specifies pixel regions on the B-mode image which are located at positions deeper than the boundary pixels as inhibition regions. The data of the coordinate positions of the inhibition regions are supplied to the image generating unit 50. As described above, according to specifying method 2, both the amniotic fluid region and the fetus regions are specified as inhibition regions.

(Specifying Method 3)

The third method is a method of specifying inhibition regions based on sizes and luminance values on a B-mode image.

Both a pixel region corresponding to an amniotic fluid region and a pixel region corresponding to a blood vessel (to be referred to as blood vessel regions hereinafter) are liquids, and hence are difficult to identify with luminance values alone. In general, on a B-mode image, an amniotic fluid region is larger in area (volume in the case of B-mode volume data) and width than a blood vessel region. In specifying method 3, the region specifying unit 60 specifies an inhibition region (only an amniotic fluid region) from the B-mode image by using this characteristic. A typical procedure for inhibition region specifying processing using specifying method 3 will be described below.

First of all, the region specifying unit 60 specifies a pixel region having low luminance values from the B-mode image. In this case, low luminance values are those smaller than the average luminance value of the image. The region specifying unit 60 then calculates the area of the specified pixel region. The size is obtained by, for example, counting the number of pixels included in the pixel region. Upon calculating the area, the region specifying unit 60 specifies this pixel region as an amniotic fluid region, if the calculated area is larger than a threshold (size threshold). If the calculated area is smaller than the threshold (size threshold), the region specifying unit 60 does not specify this pixel region as an amniotic fluid region. The data of the coordinate position of the amniotic fluid region is supplied to the image generating unit 50. As described above, according to specifying method 3, the amniotic fluid region is specified as an inhibition region.

(Specifying Method 4)

The fourth method is a method of specifying an inhibition region based on similarity to the luminance value of a pixel (start point) set in an inhibition region by the user via the operation unit 80.

As described above, an amniotic fluid region has luminance values smaller than those of a placental region and fetus region. In specifying method 4, the region specifying unit 60 specifies an amniotic fluid region from the B-mode image by using this characteristic. A typical procedure for inhibition region specifying processing using specifying method 4 will be described below.

Figure 6:
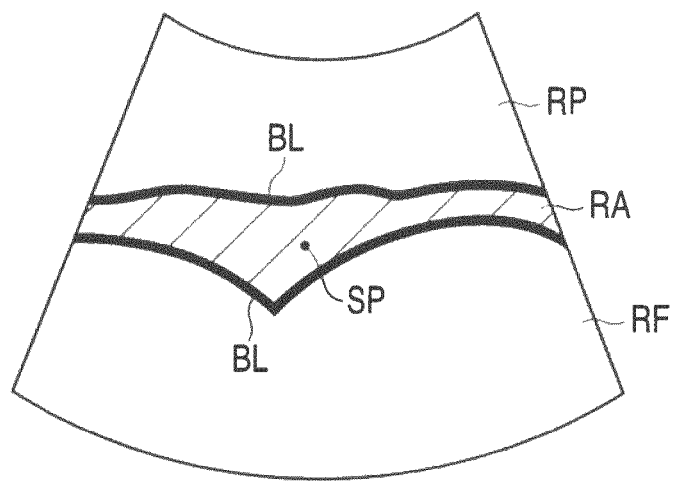
FIG. 6 is a view for explaining inhibition region specifying processing using specifying method 4, which is performed by the region specifying unit in FIG. 1.

FIG. 6 is a view for explaining inhibition region specifying processing using specifying method 4. First of all, the region specifying unit 60 sets, as a start point, a pixel SP designated in the amniotic fluid region RA on the B-mode image by the user via the operation unit 80. Upon setting the start point SP, the region specifying unit 60 searches neighboring pixels from the start point SP and integrates pixels satisfying a predetermined integration condition. An example of an integration condition is that a luminance value must be equal to or less than a threshold. This threshold is set between the minimum luminance value that the placental region RP can take and the maximum luminance value that the amniotic fluid region RA can take. When there is no pixel that can be integrated, the region specifying unit 60 specifies the integrated pixel region as the amniotic fluid region RA. The amniotic fluid region RA is the pixel region between the integrated pixel regions as boundaries BL. The data of the coordinate position of the amniotic fluid region RA is supplied to the image generating unit 50. As described above, according to specifying method 4, an amniotic fluid is specified as an inhibition region.

(Specifying Method 5)

The fifth method is a method of specifying a fetus region based on a pixel (start point) set in an inhibition region by the user via the operation unit 80 and a luminance distribution unique to the inhibition region.

Figure 7:
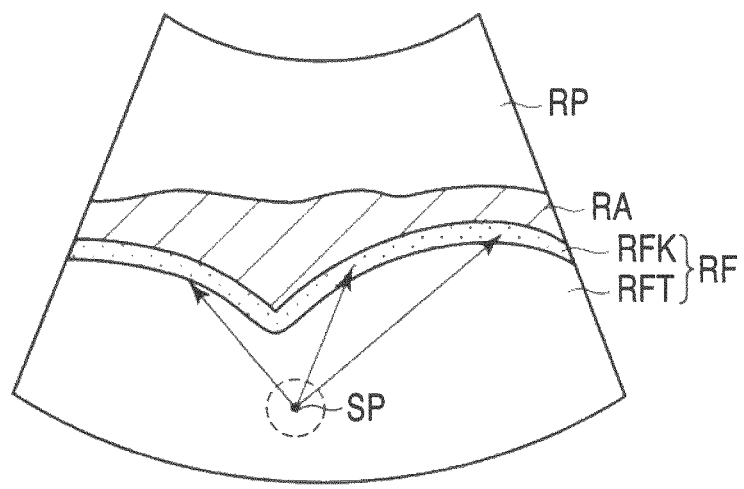
FIG. 7 is a view for explaining inhibition region specifying processing using specifying method 5, which is performed by the region specifying unit in FIG. 1.

FIG. 7 is a view for explaining inhibition region specifying processing using specifying method 5. As shown in FIG. 7, the fetus region RF can be classified into a fetus region boundary portion RFK and a fetus region internal portion RFT according to the luminance values. The fetus region boundary portion RFK has higher luminance than the fetus region internal portion RFT. The fetus region boundary portion RFK originates from a strong ultrasonic reflector such as a bone of the fetus. The region specifying unit 60 specifies an inhibition region (only a fetus region) from the B-mode image by using this characteristic. A typical procedure for processing in specifying method 5 will be described below.

First of all, the region specifying unit 60 sets, as a start point, a pixel SP designated in the fetus region internal portion RFT on the B-mode image by the user via the operation unit 80. Upon setting the start point SP, the region specifying unit 60 searches neighboring pixels from the start point SP and specifies pixels (to be referred to as high-luminance pixels hereinafter) having luminance values equal to or more than a preset threshold. This threshold is set to the minimum luminance value that the fetus region boundary portion RFK can take. That is, high-luminance pixels are those located on the fetus region boundary portion RFK. The region specifying unit 60 performs this search processing along all azimuth directions from the start point SP to specify the fetus region boundary portion RFK. Upon specifying the fetus region boundary portion RFK, the region specifying unit 60 specifies a pixel region (including the fetus region boundary portion RFK) surrounded by the fetus region boundary portion RFK as the fetus region RF. The data of the coordinate position of the fetus region RF is supplied to the image generating unit 50. As described above, according to specifying method 5, a fetus region is specified as an inhibition region.

What has been described above is inhibition region specifying processing by the region specifying unit 60.

Figure 8:
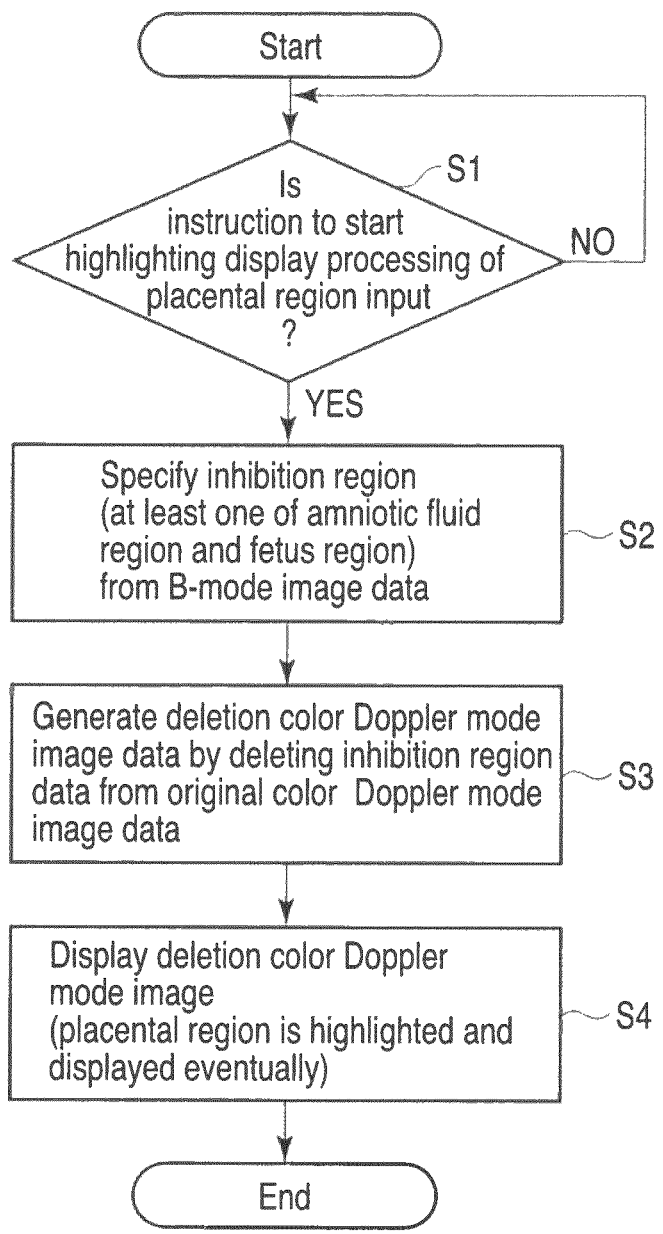
FIG. 8 is a flowchart showing a typical procedure for placental region highlighting display processing performed under the control of a system control unit in FIG. 1.

Placental region highlighting display processing performed under the control of the system control unit 100 will be described next by taking antenatal ultrasonic examination as an example. FIG. 8 is a flowchart showing a typical procedure for placental region highlighting display processing. Assume that the image generating unit 50 has already generated the B-mode image data and color Doppler mode image data of the same slice or at the same visual line position and in the same visual line direction, and the storage unit 90 has already stored the data at the start time point in step S1 in FIG. 8.

As shown in FIG. 8, in antenatal ultrasonic examination, the system control unit 100 waits for the input of an instruction to start placental region highlighting display processing by the user via the operation unit 80 (step S1). When an instruction to start is issued (YES in step S1), the system control unit 100 controls the respective units in the ultrasonic image processing apparatus 200 to start placental region highlighting display processing.

First of all, the system control unit 100 controls the region specifying unit 60 to make it perform the above inhibition region specifying processing (step S2). In step S2, the region specifying unit 60 specifies an inhibition region (at least one of an amniotic fluid region and a fetus region) on a B-mode image by using any one of specifying methods 1, 2, 3, 4, and 5 described above. The data of the coordinate position of the specified inhibition region is supplied to the image generating unit 50.

Note that as described above, the region specifying unit 60 can specify both an amniotic fluid region and a fetus region by using at least one of specifying methods 1 and 2. In addition, the region specifying unit 60 can specify an amniotic fluid region by using at least one of specifying methods 3 and 4. Furthermore, the region specifying unit 60 can specify a fetus region by using specifying method 5. When, therefore, the user wants to delete both an amniotic fluid region and a fetus region from a display image, specifying method 1 or 2 is executed in step S2. Alternatively, when the user wants to delete both an amniotic fluid region and a fetus region from a display image, at least one of specifying methods 3 and 4 and specifying method 5 are executed in step S2. When the user wants to delete only an amniotic fluid region from a display image, specifying method 3 or 4 is executed in step S2. When the user wants to delete only a fetus region from a display image, specifying method 5 is executed in step S2. A specifying processing method to be executed by the region specifying unit 60 is automatically selected or can be arbitrarily selected by the user via the operation unit 80.

Upon executing step S2, the system control unit 100 causes the image generating unit 50 to perform generating processing (step S3). In step S3, the image generating unit 50 generates the deletion color Doppler mode image data in accordance with the data of the coordinate position of the inhibition region supplied from the region specifying unit 60. More specifically, first of all, the image generating unit 50 specifies a pixel region, on the color Doppler mode image, which coincides with the coordinate position of the inhibition region supplied from the region specifying unit 60. The image generating unit 50 generates the deletion color Doppler mode image data by deleting the color Doppler mode image data assigned to the specified pixel region. The generated deletion color Doppler mode image data is supplied to the display unit 70.

The image generating unit 50 also generates the deletion B-mode image data in accordance with the data of the coordinate position of the inhibition region supplied from the region specifying unit 60. More specifically, first of all, the image generating unit 50 specifies a pixel region, on the B-mode image, which coincides with the coordinate position of the inhibition region supplied from the region specifying unit 60. The image generating unit 50 then generates the deletion B-mode image data by deleting the B-mode image data assigned to the specified pixel region. The generated deletion B-mode image data is supplied to the display unit 70. The user has made setting in advance, via the operation unit 80, concerning whether to generate the deletion B-mode image data.

Upon executing step S3, the system control unit 100 causes the display unit 70 to perform display processing (step S4). In step S4, the display unit 70 displays the deletion color Doppler mode image corresponding to the deletion color Doppler mode image data supplied from the image generating unit 50. Typically, the display unit 70 superimposes the B-mode image corresponding to the B-mode image on the deletion color Doppler mode image. In step S3, when the deletion B-mode image data is generated, the display unit 70 may display the deletion B-mode image and the deletion color Doppler mode image while superimposing the deletion B-mode image and the deletion color Doppler mode image. Note that the deletion color Doppler mode image in step S4 is equal in slice position and slice direction to the B-mode image in step S2.

Figure 9:
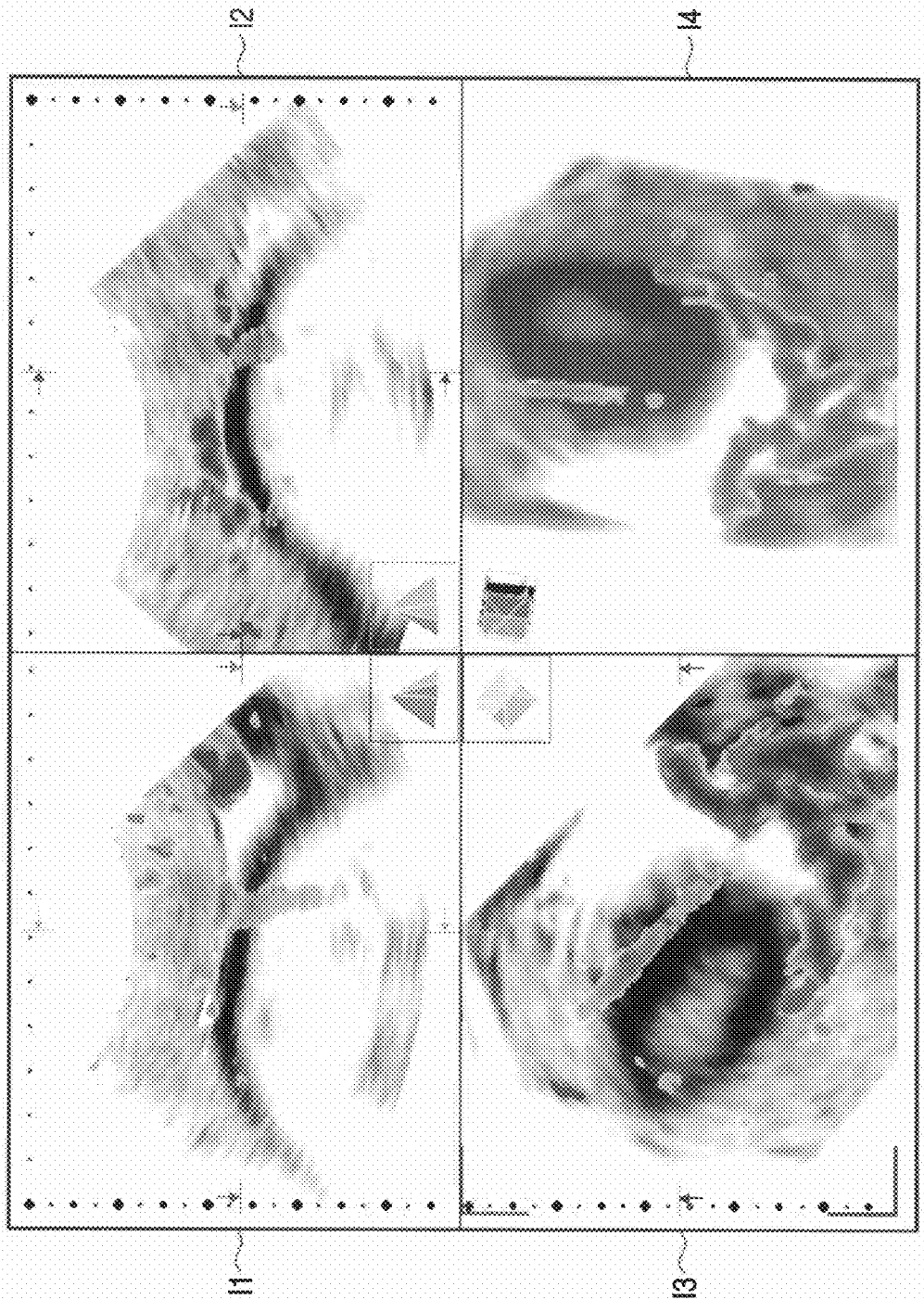
FIG. 9 is a view showing an example of a display layout in step S4 in FIG. 8.

FIG. 9 is a view showing an example of a display layout in step S4. As shown in FIG. 9, in step S4, one window displays three MPR images (deleted B-mode images) I1, I2, and I3 associated with three orthogonal slices and a three-dimensional image (deleted B-mode image) associated with a predetermined viewpoint position and a predetermined visual line direction. A deleted color Doppler mode image from which the color on the inhibition region is deleted is superimposed and displayed on each image. Since the color on the inhibition region is deleted in this manner, fluid object information associated with the inhibition region is not displayed on the deleted color Doppler mode image. This deletes the factor that inhibits the visual observation of fluid object information associated with the placental region. As a consequence, the placental region is highlighted and displayed by deleting and displaying the color associated with the inhibition region.

When observing a blood flow in a placental cortex portion on a three-dimensional image from the interior of the womb, the user sets a viewpoint position in a pixel region associated with the interior of the womb, and sets a visual line direction from the viewpoint position to the pixel region associated with the placental cortex portion. The image generating unit 50 generates the deletion color Doppler mode image data and B-mode volume image based on the set viewpoint position and visual line direction. This generates the three-dimensional image data associated with the visual line direction from the interior of the womb to the placental cortex portion.

If a color Doppler mode image is a three-dimensional image, the inhibition region data may be deleted before or after volume rendering. When deleting the inhibition region data before volume rendering, the image generating unit 50 deletes the inhibition region data from the color Doppler mode volume data. The image generating unit 50 then generates the deletion color Doppler mode image data by volume rendering of the color Doppler mode volume data from which the inhibition region data is deleted.

When, for example, a visual line position and a visual line direction are to be set again, the image generating unit 50 deletes the inhibition region data after volume rendering. This deletion method includes the first method which does not redo volume rendering and the second method which redoes volume rendering. In the first method, the image generating unit 50 generates the color Doppler mode image data by volume rendering of color Doppler mode volume data based on the reset visual line position and visual line direction. The image generating unit 50 generates the deletion color Doppler mode image data by deleting the inhibition region data from the generated color Doppler mode image data.

In the second method, the image generating unit 50 generates the deletion color Doppler mode image data by volume rending of the color Doppler mode volume data from which the inhibition region data is deleted based on the reset visual line position and visual line direction.

In addition, according to an application of step S4, the display unit 70 has a function of automatically displaying a three-dimensional B-mode image allowing easy observation of a placental region, when an inhibition region is specified. More specifically, first of all, the image generating unit 50 specifies the surface of a placental region included in B-mode volume data, and specifies a visual line direction based on the specified surface. For example, a visual line direction is specified in a direction perpendicular to a surface in the placental region. The image generating unit 50 generates three-dimensional B-mode image data associated with the specified visual line direction by volume rending of B-mode volume data based on the specified visual line direction. The image generating unit 50 generates three-dimensional image data from which luminance corresponding to an inhibition region is deleted. The display unit 70 displays a three-dimensional image corresponding to the generated three-dimensional image data. The displayed three-dimensional image is from which the luminance corresponding to the inhibition region is deleted. This displays the three-dimensional image with a placental surface facing the display surface. Therefore, the user can easily check the form of a placental surface and fluid object information from which an inhibition region is concealed.

When step S4 is complete, the system control unit 100 terminates the highlighting display processing of the placental region.

As described above, when displaying a placental region on a color Doppler mode image, the ultrasonic diagnosis apparatus, ultrasonic image processing apparatus, and ultrasonic image processing program according to this embodiment delete fluid object information generated in an inhibition region in an amniotic fluid region, a fetus region, or the like. This can therefore delete fluid object information that visually inhibits fluid object information generated in a placental region on a color Doppler mode image. As a consequence, the fluid object information generated in the placental region is highlighted and displayed. Relatively highlighting a placental region in this manner clinically facilitates checking an intraplacental blood flow, a blood flow in a placental cortex portion, and the presence/absence of a disease such as an arteriovenous shunt regardless of a blood flow in the fetus, the movement of an amniotic fluid accompanying the movement of the fetus, and the like. This technique prevents mixture of fluid object information associated with the placenta with fluid object information associated with amniotic fluid or the interior of a fetus on a color Doppler mode image. This can therefore improve the image diagnosis accuracy associated with antenatal ultrasonic examination by a user such as a doctor.

In this embodiment, it is possible to delete inhibition regions such as an amniotic fluid region and a fetus region on a B-mode image. Since it is possible to delete a fetus region which visually inhibits a placental region on a B-mode image, even if the fetus is close to the placenta, it is easy to observe the placental region. Deleting an inhibition region from a B-mode image clinically facilitates the observation of the form of a placental surface. This therefore facilitates the observation of the form of the placenta, thus improving the image diagnosis accuracy associated with antenatal ultrasonic examination by the user. In addition, a user such as a doctor can perform antenatal ultrasonic examination of the interior of the womb without bothering to change the slice or the visual line as in the prior art.

The ultrasonic diagnosis apparatus, ultrasonic image processing apparatus, and ultrasonic image processing program according to this embodiment achieve an improvement in image diagnosis accuracy in placental ultrasonic examination. Accompanying this, the image diagnosis time is shortened.

Note that each function associated with this embodiment can also be implemented by installing the ultrasonic image processing programs for executing the corresponding processing in a computer such as a workstation and mapping them in a memory. In this case, the image processing programs which can cause the computer to execute the corresponding techniques can be distributed by being stored in recording media such as magnetic disks (Floppy® disks, hard disks, and the like), optical disks (CD-ROMs, DVDs, and the like), and semiconductor memories.

(Modification)

This embodiment specifies an inhibition region on a B-mode image. A modification of the embodiment specifies an inhibition region on a color Doppler mode image. More specifically, the region specifying unit 60 according to the modification specifies, as a fetus region, a region (a pixel region associated with clutter components) associated with the fetus under operation in a color Doppler mode image. The data of the coordinate position of the specified fetus region is supplied to the image generating unit 50. The image generating unit 50 generates deletion color Doppler mode image by deleting fetus region data from the color Doppler mode image data. The fetus region data corresponds to the fetus region. In addition, the image generating unit 50 generates deletion B-mode image data by deleting luminance from the B-mode image data. The deleted luminance corresponds to the fetus region. The generated deletion color Doppler mode image data and the deletion B-mode image data are supplied to the display unit 70. The display unit 70 displays a deletion color Doppler mode image corresponding to the supplied deleted color Doppler mode image without any change, or superimposes and displays it on the B-mode image or the deletion B-mode image. This can remove a region, of the fetus region, which is under operation from the color Doppler mode image or the B-mode image.

While certain embodiments have been described, these embodiments have been presented by way of example only, and are not intended to limit the scope of the inventions. Indeed, the novel embodiments described herein may be embodied in a variety of other forms; furthermore, various omissions, substitutions and changes in the form of the embodiments described herein may be made without departing from the spirit of the inventions. The accompanying claims and their equivalents are intended to cover such forms or modifications as would fall within the scope and spirit of the inventions.

What is claimed is:

1. An ultrasonic diagnosis apparatus, which executes B-mode scanning and color Doppler mode scanning on a scanning region associated with an interior of the womb of a pregnant woman via an ultrasonic probe, the apparatus comprising:
    processing circuitry configured to
        generate a first color Doppler mode image associated with the scanning region based on an output from the ultrasonic probe at the time of the color Doppler mode scanning and generate first B-mode image associated with the scanning region based on an output from the ultrasonic probe at the time of the B-mode scanning;
        specify a specific region, including at least one of an amniotic fluid region and a fetus region and excluding a placenta region, based on a luminance distribution of the first B-mode image;
        generate a second color Doppler mode image by deleting a part of the first color Doppler mode image corresponding to the specific region from the first color Doppler mode image, the second color Doppler mode image representing a blood flow in a region excluding the specific region;
        generate a combined image by superimposing the second color Doppler mode image and the first B-mode image, wherein a color Doppler mode image is absent and a B-mode image is present in the specific region of the combined image; and
        control display of the combined image on the display.

2. The apparatus according to claim 1, wherein the processing circuitry is further configured to
    generate a second B-mode image by deleting a part from the first B-mode image, the part from the first B-mode image corresponding to the specific region; and
    control display of a color Doppler mode image and the second B-mode image while superimposing the color Doppler mode image and the second B-mode image.

3. The apparatus according to claim 1, wherein the processing circuitry is further configured to specify the specific region from the first B-mode image based on one of a signal intensity distribution and a luminance distribution unique to the specific region.

4. The apparatus according to claim 1, wherein the processing circuitry is further configured to calculate, for each of a plurality of local regions on the first B-mode image, an index representing one of a signal intensity distribution and a luminance distribution in the local region, and specifies the specific region based on the index.

5. The apparatus according to claim 1, wherein the processing circuitry is further configured to specify the specific region based on a position and one of a signal intensity and a luminance value on the first B-mode image.

6. The apparatus according to claim 1, wherein the processing circuitry is further configured to specify the specific region based on one of a signal intensity and a luminance value and a size of a region on the first B-mode image.

7. The apparatus according to claim 1, wherein the processing circuitry is further configured to specify the specific region based on a similarity to one of a signal intensity and a luminance value of a specific pixel set in the specific region on the first B-mode image in accordance with an instruction from a user.

8. The apparatus according to claim 1, wherein the processing circuitry is further configured to specify the specific region based on a specific pixel set in the specific region on the first B-mode image and one of a signal intensity distribution and a luminance distribution unique to the specific region on the first B-mode image in accordance with an instruction from a user.

9. The apparatus according to claim 1, wherein the processing circuitry sets a viewpoint position of the combined color Doppler mode image and B-mode image to be in a pixel region associated with the interior of the womb, and direct a visual line direction of the combined color Doppler mode image and B-mode image from the viewpoint position to a pixel region associated with a placental cortex portion of the pregnant woman.

10. An ultrasonic image processing apparatus, comprising:
    a storage configured to store a first B-mode image and a first color Doppler mode image associated with an interior of the womb of a pregnant woman; and
    processing circuitry configured to
        specify a specific region including at least one of an amniotic fluid region and a fetus region and excluding a placenta region based on a luminance distribution of the first B-mode image;
        generate a second color Doppler mode image by deleting a part of the first color Doppler mode image corresponding to the specific region from the first color Doppler mode image, the second color Doppler mode image representing a blood flow in a region excluding the specific region;
        generate a combined image by superimposing the second color Doppler mode image and the first B-mode image, wherein a color Doppler mode image is absent and a B-mode image is present in the specific region of the combined image; and
        control display of the combined image on the display.

11. The apparatus according to claim 10, wherein the processing circuitry is further configured to
    generate second B-mode image by deleting a part from the first B-mode image, the part from the first B-mode image corresponding to the specific region; and
    control display of a color Doppler mode image and the second B-mode image while superimposing the color Doppler mode image and the second B-mode image.

12. The apparatus according to claim 10, wherein the processing circuitry sets a viewpoint position of the combined color Doppler mode image and B-mode image in a pixel region associated with the interior of the womb, and directs a visual line direction of the combined color Doppler mode image and B-mode image from the viewpoint position to a pixel region associated with a placental cortex portion of the pregnant woman.

13. An ultrasonic image processing method, comprising:
    specifying, by processing circuitry, a specific region including at least one of an amniotic fluid region and a fetus region and excluding a placenta region based on a luminance distribution of a first B-mode image associated with an interior of the womb of a pregnant woman;
    generating, by the processing circuitry, an output color Doppler mode image by deleting a part of the output color Doppler mode image corresponding to the specific region from an original color Doppler mode image associated with the interior of the womb, the output color Doppler mode image representing a blood flow in a region excluding the specific region;
    generating, by the processing circuitry, a combined image by superimposing the output color Doppler mode image and the first B-mode image on a display, wherein the output color Doppler mode image is absent and a B-mode image is present in the specific region of the combined image; and controlling display of the combined image on the display.

14. The method according to claim 13, further comprising:

generating a second B-mode image by deleting a part from the first B-mode image, the part from the first B-mode image corresponding to the specific region; and displaying a color Doppler mode image and the second B-mode image while superimposing the color Doppler mode image and the second B-mode image.

15. The method according to claim 13, wherein a viewpoint position of the combined color Doppler mode image and B-mode image is set in a pixel region associated with the interior of the womb, and a visual line direction of the combined color Doppler mode image and B-mode image is directed from the viewpoint position to a pixel region associated with a placental cortex portion of the pregnant woman.

16. A non-transitory computer readable medium storing thereon an ultrasonic image processing program that, when executed by processing circuitry of a computer, causes the computer to, specify a specific region including at least one of an amniotic fluid region and a fetus region excluding a placenta region based on a luminance distribution of a B-mode image associated with an interior of the womb of a subject;

generate an output color Doppler mode image by deleting a part of a first color Doppler mode image corresponding to the specific region from an original color Doppler mode image associated with the interior of the womb, the output color Doppler mode image representing a blood flow in a region excluding the specific region;

generate a combined image by superimposing the output color Doppler mode image and the B mode image, wherein a color Doppler mode image is absent and a B-mode image is present in the specific region of the combine image; and control display of the combined image on the display.

17. An ultrasonic diagnosis apparatus, which executes B-mode scanning and color Doppler mode scanning on a scanning region associated with an interior of the womb of a pregnant woman via an ultrasonic probe, the apparatus comprising:

processing circuitry configured to generate a first color Doppler mode image associated with the scanning region based on an output from the ultrasonic probe at the time of the color Doppler mode scanning and generate a B-mode image associated with the scanning region based on an output from the ultrasonic probe at the time of the B-mode scanning;

specify a fetus region excluding a placenta region by using the first color Doppler mode image;

generate a second color Doppler mode image by deleting a art of a color Doppler mode image corresponding to the fetus region from the first color Doppler mode image, the second color Doppler mode image representing a blood flow in a region excluding the fetus region;

generate a combined image by superimposing the second color Doppler mode image and the B-mode image, wherein a color Doppler mode image is absent and a B-mode image is present in the fetus region of the combine image; and control display of the combined image on the display.

18. An ultrasonic image processing apparatus, comprising:

a storage configured to store a B-mode image and first a color Doppler mode image associated with an interior of the womb of a pregnant woman; and processing circuitry configured to specify a fetus region excluding a placenta region by using the first color Doppler mode image;

generate a second color Doppler mode image by deleting a part of a color Doppler mode image corresponding to the fetus region from the first color Doppler mode image, the second color Doppler mode image representing a blood flow in a region excluding the fetus region;

generate a combined image by superimposing the second color Doppler mode image and the B-mode image, wherein a color Doppler mode image is absent and a B-mode image is present in the fetus region of the combine image; and control display of the combined image on the display.

19. A non-transitory computer readable medium storing thereon an ultrasonic image processing program that, when executed by processing circuitry of a computer, causes the computer to:

specify a fetus region excluding a placenta region by using a first color Doppler mode image associated with an interior of the womb of a pregnant woman;

output a color Doppler mode image by deleting a part of a color Doppler mode image corresponding to the fetus region from the first color Doppler mode image, the color Doppler mode image representing a blood flow in a region excluding the fetus region;

generate a combined image by superimposing the output color Doppler mode image and a B-mode image, wherein a color Doppler mode image is absent and a B-mode image is present in the fetus region of the combine image; and control display of the combined image on the display.

* * * * *